United States Patent [19]

Zartman

[11] E Patent Number: Re. 32,758

[45] Reissued Date of Patent: Oct. 4, 1988

[54] METHOD FOR REMOTELY MONITORING THE LONG TERM DEEP BODY TEMPERATURE IN FEMALE MAMMALS

[75] Inventor: David L. Zartman, Worthington, Ohio

[73] Assignee: New Mexico State University Foundation, Inc., Las Cruces, N. Mex.

[21] Appl. No.: 744,636

[22] Filed: Jun. 14, 1985

Related U.S. Patent Documents

Reissue of:

[64] Patent No.: 4,387,724
Issued: Jun. 14, 1983
Appl. No.: 149,250
Filed: May 12, 1980

[51] Int. Cl.[4] ..... A61B 10/00
[52] U.S. Cl. ..... 128/736; 128/738
[58] Field of Search ..... 128/736, 738, 130, 131, 128/127

[56] References Cited

U.S. PATENT DOCUMENTS

| | | | |
|---|---|---|---|
| 3,156,117 | 10/1964 | Benzinger | 128/736 |
| 3,781,837 | 12/1973 | Anderson | 128/736 |
| 3,811,423 | 5/1974 | Dickinson et al. | 128/1 R |
| 3,811,424 | 5/1974 | Dickinson et al. | 128/1 R |
| 3,844,273 | 10/1974 | Polson | 128/738 |
| 3,893,111 | 7/1975 | Cotter | 343/718 X |
| 4,028,687 | 6/1977 | Hamaguchi et al. | 340/870.16 |
| 4,031,365 | 6/1977 | Raggiotti et al. | 364/557 |
| 4,119,089 | 10/1978 | Preti et al. | 436/65 |
| 4,148,304 | 4/1979 | Mull | 128/736 |
| 4,312,360 | 1/1982 | Conway et al. | 128/736 |
| 4,387,724 | 6/1983 | Zartman | 128/736 |

OTHER PUBLICATIONS

Singer, A. "An Automatic System for Measuring & Recording of BBJ in the Human Female", *Fertility & Sterility,* 15:44–51 (1964).

K. Maatje and W. Rossing, "Detecting Oestrus by Measuring Milk Temperatures of Dairy Cows During Milking," (from *Livestock Production Science*) 1975, from The Netherlands, pp. 85 to 89.

"Calving Signs You Can Use", *Hoard's Dairyman,* 101:1188, 1956 by Melvin Scholl.

"Heat-Tolerance Studies of Fat-Tailed Sheep in the Subtropics", *J. Agr. Sci.,* 47:280–286, 1956 by E. S. E. Hafez et al.

"Vaginal Temperature of Cows Before and After Calving", *JAVMA* 131:381–383, 1957 by I. D. Porterfield, Ph.D. et al.

Report of the New York State Veterinary College at Cornell University, 1962–1963, S. J. Roberts reference, p. 93.

"The Fall in Rectal Temperature Seen Before Parturition in Sheep", *J. Reprod. Fert.* (1969), 19, 569–571, by R. Ewbank.

"Flucuations in Rectal Temperature of Swine at Parturition," *Canadian Veterinary Journal,* 13:72–74 (1972), G. J. King et al.

"Reproduction in the Dog and Cat", *Reproduction in Domestic Animals,* 3d Ed. Acedemic Press, NY, p. 665, H. H. Cole, 1977.

"Predicting the Time of Parturition in the Normal Cow . . . ", *The Veterinary Record,* vol. 75, No. 14, by R. Ewbank.

"An Autom. System for Meas. & Recording of BBT in the Human Female", *Fertility and Sterility,* 15: 44–51, (1964), by Singer.

"Ireless Fever Alarm Device", *Med. Biol. Engrg. & Computing,* 1979, vol. 17, pp. 550–552, by Kingma et al.

"Continuously Telemetered Vaginal Temp. in the Baboon", *The Baboon in Med. Res., IIed.,* Univ. of Texas Press, Austin, (1967), pp. 19–35 by Hendrikx et al.

"Meas. of Elec. Res. & Temp. in Vaginal Mucosa of the Sows During Estrous", Veterinary Bulletin, 48: 261, (1978) by Michael.

"The Association Between Basal Body Temperature, Sexual Swelling, and Urinary Gonadal Hormone Levels in Menstral Cycle of the Chimpanzee", *Jrnl. of Reprod. Fertility,* 1977, vol. 50, pp. 23–28 by Graham et al.

*Primary Examiner*—Francis J. Jaworski
*Attorney, Agent, or Firm*—Lane & Aitken

[57] ABSTRACT

This invention relates to a novel method for remotely detecting and monitoring on a long term basis the deep body temperature of a mammalian female which comprises the steps of attaching a temperature-sensing probe capable of remote interrogation to an expandable anchor, implanting the probe with the anchor attached thereto in collapsed condition within the vaginal canal, expanding the anchor to maintain the probe in place despite the animal's muscular efforts to expel same, interrogating the probe from a remote location on a daily basis at approximately the same time each day for a period not less than one complete estrous cycle, and noting any abrupt change in temperature within each cycle as an indication of physiological stress.

8 Claims, 7 Drawing Sheets

MARE I (INTRAVAGINAL)

Figure 1:
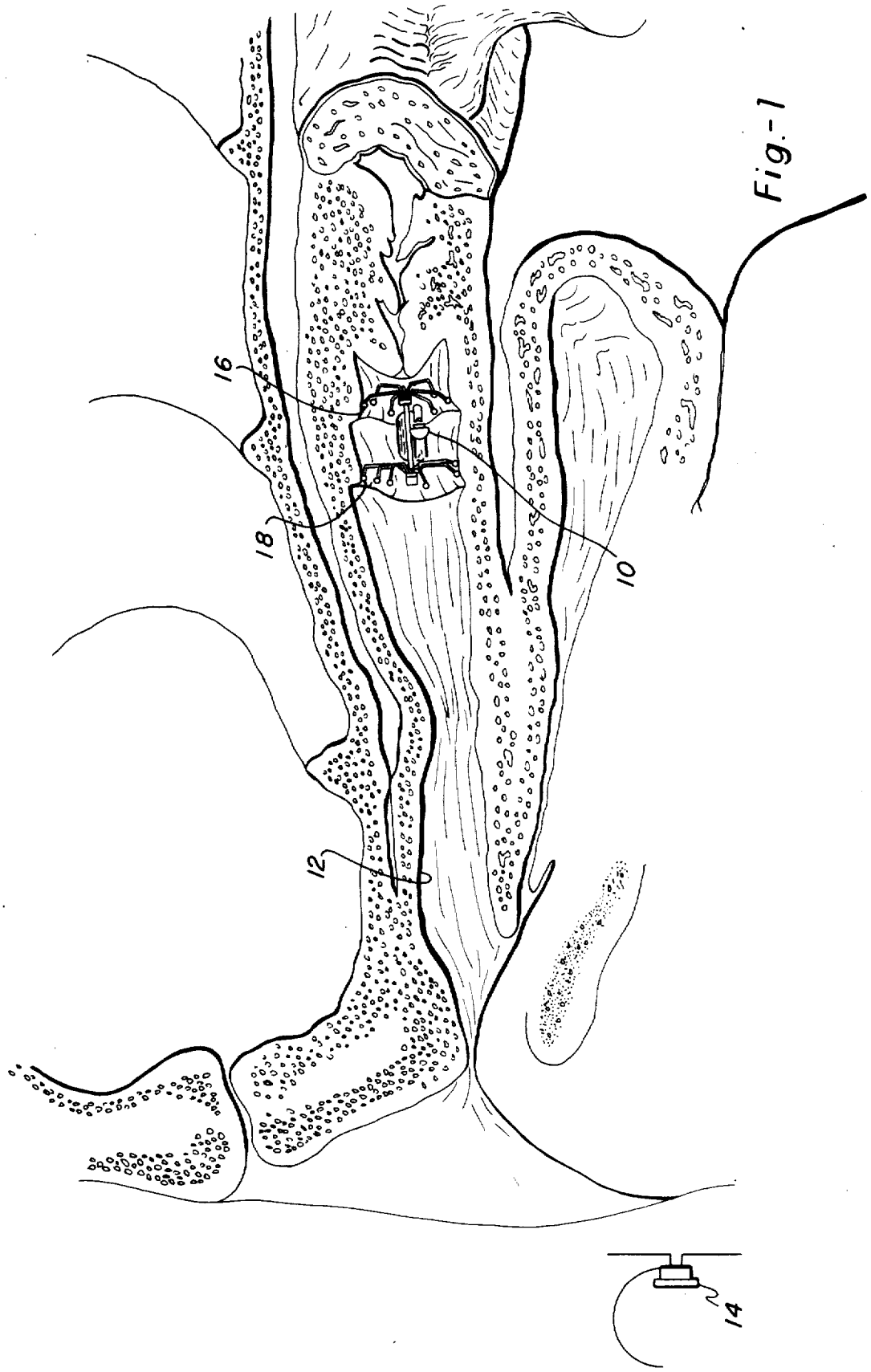

27 DAYS
23 DAYS
20 DAYS
A
B
C
D
HEAT
HEAT
HEAT
xxx
1050
1040
1030
5 Min
1020
1010
1000
10
20
30
40
60
70
80
90
100
DAYS
Began 9 May, 1979

MARE II (INTRAVAGINAL)

35 days
9 days
23 days
A
B
C
D
K
HEAT
HEAT
HEAT
Began 1 April, 1979
900
890
880
5 Min
870
860
850
840
10
20
30
40
60
70
80
DAYS

SOW (INTRAVAGINAL)

HEIFER 1474 (INTRAVAGINAL)

HEAT
21 DAYS
19 DAYS
HEAT
16 DAYS
29 DAYS
HEAT
HEAT
A
B
C
D
1060
1050
1040
1030
5 Min
1020
1010
1000
990
10
20
30
40
DAYS
60
70
80
90
100
Began 17 April, 1979

HEIFER 1494 (INTRAVAGINAL)

1110
1100
1090
1080
1070
1060
5 Min
1050
1040
1030
1020
1010
A
B
C
HEAT
20 DAYS
23 DAYS
Began 21 May, 1979
10
20
30
DAYS
50
60
70

INFERTILE COW 690 (INTRAVAGINAL)

850
840
830
820
5 Min
810
800
790
780
A
420
B
957
HEAT ?
HEAT
X
10
20
30
40
DAYS
60
70
80
90
100
Began 23 July, 1979

METHOD FOR REMOTELY MONITORING THE LONG TERM DEEP BODY TEMPERATURE IN FEMALE MAMMALS

Matter enclosed in heavy brackets [ ] appears in the original patent but forms no part of this reissue specification; matter printed in italics indicates the additions made by reissue.

Livestock breeders, especially cattlemen, find that one of their major concerns is that of being able to maximize the conception rate of their females. A conception percentage of 80% or above is considered good. In the dairy industry where husbandry is practiced more intensively than in ordinary beef production, [diarymen] *dairymen* consider that a poor conception rate is one of their most significant management as well as economic problems. The root of the problem is basically the failure to reliably detect estrus. This is especially significant in the dairy industry because dairy cattle are, for the most part, hand bred and the herd manager or operator must know when to introduce the cow to a bull or else inseminate her artificially. As valuable a tool as artificial insemination is to the dairy industry and others, it is being used far less than it should be because of the difficulties associated with detecting estrus, some of which at least can be solved by a bull in conjunction with an assortment of commercially available detection aids which provide visual evidence of when the bull has mounted the cow.

A cow that has not become pregnant within 80 days after calving costs the dairyman in excess of two dollars per day in lost income and actual out of pocket expenses. The cow who exhibits abnormal reproductivity, on the other hand, can easily go undetected for even a much longer period of time.

Apart from using the bull, stallion or boar as a means in and of himself or in conjunction with some artificial aid to detect ovulation, much attention has been given to the detection of abnormal body temperatures, even in humans. For the most part, the detection of temperature changes in bovines and equines has, up until recently, been reliant upon standard temperature probes such as ordinary thermometers that were temporarily inserted by hand into the rectum or vulva for the brief interval required to get a reading and then removed. Obviously, such a technique requires confinement of the animal and a great deal of time and effort on the part of some human being. This labor-intensive effort is completely impractical for use over the extended period of time required to develop a temperature history for the animal adequate to use as a basis for noting any anomalous state of affairs.

Early illness detection presents yet another problem because, ordinarily, the animal does not have her temperature checked until overt signs of physical illness have become apparent to the observer. This is often hours, if not days, after the onset of the illness thus necessitating a longer recovery, greater expense and other undesirable consequences. In the dairy herd, rapid illness detection becomes especially significant due to the decreased milk output, possible drug contamination of the milk, reduction in feed conversion efficiency, etc.

It has been recognized for quite a long time that various significant physiological changes in female mammals, including the human species, could be detected through change in deep body temperature before other external manifestations provided any clue to what was taking place. Ovulation in human females can, for example, be detected in some women by a careful monitoring of their body temperature and such a procedure is in rather widespread use as a birth control system. While the so-called "basal body temperature" (BBT) has been known for a long time to bear an important correlation to the menstrual cycle of a human female, it has also been found that the usual oral and rectal methods of measuring body temperatures lack the precision necessary to detect the rather minute incremental changes that signify the onset of ovulation. In an effort to solve this problem and measure the BBT in the human female with greater precision, Dr. John H. Mattox et al. implanted accurate temperature sensing instruments intravaginally in a number of women. These instruments telemetered the BBT to remote data collection stations which monitored it and compared the results over several menstrual cycles with similar BBT's taken orally. The results of this study were published in Volume 27, No. 9 dated September 1976 of the reports of the American Fertility Society following presentation of a paper on the subject in October 1975 at the Annual Meeting of the Pacific Coast Fertility Society.

While the foregoing study clearly demonstrated the practicality of telemetering deep body temperature data to a remote data collection station from a site within the vaginal canal of a human female, it also clearly showed how complex such a system is and how much cooperation on the part of the participants was necessary in order to provide the investigators with reliable data. Also, not one of the women who participated in the study left the temperature probe implanted more than a few hours out of each day and, while the investigators felt that the "cumbersome and complex" system could probably be simplified, they agreed that their study using an intravaginal probe did little more than establish the worth of the conventional oral temperature method as a means for detecting ovulation. Clearly, a system such as that employed by Dr. Mattox was unsuitable for livestock since the study demanded a great deal of intelligent cooperation on the part of each participant which an animal is totally incapable of providing.

[Diarymen] *Dairymen* have known for years that a cow's body temperature is capable of foretelling the onset of estrus as well as conditions of poor health like, for example, mastitis and other fever-inducing ailments. They also knew that a cow's temperature varied greatly with ambient conditions and were by no means the same from one animal to the next even under identical conditions thus, while it has been recognized that a long term temperature history of a particular cow related to the change in ambient conditions should be very helpful in detecting the small abnormalities in the temperature profile for a given animal that are needed for a reliable prediction of estrus or a febrile illness, no way was known in 1978 for obtaining such information as reported in Hoard's Dairyman by Armstrong and Wiersma; 123(13): 823, July 10, 1978. These authors reported attempts at measuring milk temperatures and analogous body temperatures predicated upon the latter but the clear conclusion was reached that "It is apparent that the use of cow body or milk temperature for early detection of mastitis, estrus or illness has little value under Arizona conditions." This same article alluded to a study in The Netherlands when monitoring the milk temperature in the claw-piece of the milker was effective in detecting estrus in 16 out of 19 cows based upon a 0.5° change; however, these authors seriously doubted whether deviations of this order of magnitude and less would be effective under the conditions they were working under in Arizona and their conclusion was that they would not. Even before Armstrong and Wiersma were conducting their milk temperature experiments on dairy herds in Arizona, others had experienced much the same thing in connection with different types of temperature measurements in dairy cattle.

During roughly the same period in which Dr. Mattox and his associates were making the deep body temperature study on the human female, others were attempting to use intracranial temperature measurements taken in the ear canal of dairy cattle to provide better reproductive management. M. Lira et al. reported the results of their study at the annual meeting of the American Dairy Science Association held at Kansas State University in Manhatten, Kans. during June of 1975. As was the case with the Mattox study on human females, the ear canal probes were inserted and removed on a daily basis rather than being implanted and left in place over a prolonged period of time, say a complete estrous cycle or longer. The readings that were taken were confined to the day of estrus and six days before and after. The data taken during this study revealed that the temperature of the animal was elevated very slightly and was significantly different ($P<0.01$) on the day of estrus and that the ear canal measurement coincided closely with that taken rectally. One is forced to conclude that whether the body temperature is taken rectally or intracranially, it must be taken quite accurately to detect a change in the order of a tenth of a degree. Common sense dictates that many factors, both external and internal, could be responsible for such a slight change and, for this reason, little reliance can be placed upon the detection of a change of this order of magnitude.

Various investigators at Los Alamos Scientific Laboratory operating under a contract from the U.S. Department of Energy have conducted extensive tests over the past several years on the telemetering of body temperature data and other information from livestock carrying both self-contained battery-operated transmitters and AC powered ones. Among other publications, the Holm et al. Progress Report LA-7642-PR entitled "Electronic Identification" of May 1979 summarizing work done between Oct. 1, 1977 and Sept. 30, 1978 provides one with a fairly comprehensive summary of these activities which were, for the most part, focused upon what would be required in a cost-effective system that could be implemented on a national basis to trace the movement of livestock, their physical condition, location, and other factors such as stress and estrus that would be of assistance to the industry in terms of herd management, disease control, reproduction and the like. For present purposes, this research is significant in that it did provide long term assessment of the body temperature of animals using so-called "on board" telemetry equipment capable of being monitored at a remote site. So far as is reflected from the above report, the nearest approach to deep body temperature readings that were taken came from transponders implanted surgically subdermally. While body temperatures were measured intracranially within the ear canal as had been done in the past, these readings do not qualify as deep body temperature readings nor do those taken rectally. As such, there is no teaching of any long term monitoring of deep body temperatures within a natural body cavity like, for instance, the vaginal canal of a female animal such as a cow, mare or sow.

Essentially, the foregoing publications reflect the state of the art with respect to the detection and monitoring of deep body temperatures in mammalian females for any purpose as well as for the specific purposes of recognizing the onset of illness, estrus or other similar physiological stress. Before proceeding with a description of the novel method for detecting the onset of estrus or febrile illness by means of the intravaginal measurement of deep body temperatures in female mammalian livestock that constitutes the subject matter of the instant invention it would, perhaps, be helpful to look briefly at why such information is important to the commercial livestock industry, the dairy industry and horse breeders, among others.

Take, for instance, the dairy industry which can be considered representative of similar situations existing in each of the others. It can be shown that losses due to poor reproduction alone accounted for losses totalling over a half billion dollars some ten years ago and in the present state of the argicultural industry, these losses are sure to be much greater. These losses are broken down into three broad areas as follows:

(1) Loss of production—milk and calves,
(2) Replacement costs, and
(3) Additional breeding costs (vet services and medication).

With respect to the first of these, as of ten years ago a fair consensus taken from recognized agricultural economists indicated losses to the dairyman of about 70 cents per day resulted for each day beyond the optimal yearly calving interval that a cow did not conceive. Since the optimal yearly calving interval is recognized to be twelve months and the yearly average back in 1970 was 13.5 months, the nationwide loss to the dairy industry in the United States which numbers some twelve and a half million cows represents a loss of just under $400,000 annually.

Add to the above the replacement cost factor nationally even back in 1970 of a little less than $94,000,000. These losses were occasioned by the fact that somewhere near 5% of the cows had to be slaughtered because of their failure to conceive within a reasonable time or at all coupled with the difference of around $150.00 per animal that the dairyman had to absorb as the disparity between the salvage value of the animal slaughtered and her replacement.

A similar analysis will reveal that in excess of $50,000,000 more is spent on the increased number of average services per unproductive cow that are required in the attempt to successfully breed her and the unusually high vet bills required for such an animal. A significant reduction in these losses could be realized by a reliable early detection of estrus in these animals accompanied by promptly breeding them for calving at the recommended twelve month time interval. Significant losses can also be demonstrated for both beef cattle and hogs. While the horse breeding industry has different economic problems; nevertheless, an early and reliable detection of estrus in the mare can prove to be of substantially financial advantage.

In addition to the significant economic losses occasioned by inefficient breeding, infection and metabolic stress are equally costly problems. Looking again at the dairy industry for an idea of the magnitude of these problems, it can be shown that common dairy herd diseases like mastitis, ketosis and milk fever accounted a decade ago for losses well in excess of a half billion dollars; yet, prospects are favorable for cutting these losses almost in half by merely detecting these diseases in the sub or preclinical stage before they progress to the clinical stage where they manifest themselves in a way that they can be detected by the usual methods. Early detection of febrile illness holds good promise of prompt treatment and a favorable prognosis that shortens the physical setback and restores the animal to full production before her milk output is adversely affected, at least to the degree it would be if the disease were allowed to progress further.

For the most part, cows and sows are bred artificially, therefore, the best natural means, namely the bull or boar, for detecting when the female is in heat are not available thus necessitating some other method for detecting estrus. This is not to say that accurate estrus detection is not also worthwhile in natural breeding. Take for example, horses which are bred naturally. Stud fees are generally based upon the stallion having to service the mare three or four times to insure that she is pregnant. If, on the other hand, he had to stand only once for each mare and could, therefore, service several, the stud fees could be reduced to a considerable degree. In the case of sows, they are known to exhibit no external signs of being in heat on occasion and, therefore, even the boar is no help under such circumstances.

Thus, while accurate body temperature measurements are known to provide a reliable indication of both estrus and the onset of febrile illnesses in mammalian females, both human and animal, no one has yet developed a system for reliably ascertaining this condition, especially with animals under practical herd management conditions. It has also been discovered in accordance with the teaching of the instant invention that animals differ in their body temperature patterns from humans and, therefore, absolute or "spot" readings cannot be relied upon in animals but rather only the change in temperature from one day to the next recorded at approximately the same time each day and over an extended period of time, preferably one that encompasses more than one estrous cycle. Moreover, small as the changes are, if accurately measured they are capable of differentiating between the onset of an illness and estrus, the former generally being of greater magnitude than the latter while the latter is the shorter-lived of the two.

Temperature measuring instruments, even those sufficiently small to be implanted, having the requisite accuracy present no problem as they are commercially available in the marketplace as is the radio-telemetry support system capable of transferring the "onboard" temperature data to a remote receiving station. While the cost effectiveness and longevity of such a system may prevent its being used on a widespread basis in range cattle for sometime yet as evidenced by the Los Alamos study, nevertheless, the potential saving to the dairyman, hog farmer and other breeder of farm animals as opposed to range stock can be very significant. The real challenge is not the equipment but rather the method employed to accurately measure and monitor the body temperature of the animal in such a way and at such a site that it will reliably provide the desired temperature data from which accurate predictions as to the state of health and/or ability of the animal to conceive can be made. The Mattox study previously mentioned apparently demonstrated the inapplicability of the human intravaginal implantation method to female animals since the system was so complex and cumbersome that even the supposedly "intelligent" human species failed to produce the expected results. Intracranial implantations in the ear canal proved less than effective in addressing the accurate temperature readings necessary for a reliable prediction of estrus or state of ill health as did the notoriously old rectal method. Even the surgical implantation of the radio telemetry equipment was fraught with serious deficiencies, not the least of which is the implantation itself. Nevertheless, the indications were that only deep body temperature measurements were sufficiently free of ambient climatic factors and other external influences to a point where the necessary degree of accuracy was attainable under herd management conditions. Also, as a practical matter, relatively long term implants appeared to be necessary since the herd owner could ill afford the labor cost of having to take the deep body temperature of each individual animal separately at least once a day and preferably at the same time. Another unknown factor was, of course, the traumatic effect such a daily procedure might have on the animal which might manifest itself in a brief rise in body temperature thus providing a false indication of estrus or the onset of some illness.

With these limitations in mind and knowing that neither the ear canal or the rectum provided the answer, the best possibility seemed to be the vaginal canal despite the indications to the contrary experienced by Mattox with his human subjects or, perhaps, intrauterine placement. Both of these internal sites held promise of providing a true deep body temperature reading essentially unaffected by external conditions. Also, following insemination, there appeared to be no reason for removing the temperature probe and associated radio telemetry apparatus until the time came for the animal to give birth. Furthermore, by leaving the probe in place from insemination to parturition, a long history of estrous cycles would be available for each animal on an individual basis in case the response happened to vary from one animal to another, seasonally or for some other reason.

Accordingly, it was decided to implant the probes and associated telemetry equipment within the vagina of cows, mares and sows to see if sufficiently accurate deep body temperatures could be remotely sensed to provide the investigator with a reliable indication of just when estrus or some other physiological change manifesting itself in a rise or lowering of body temperature took place. Unfortunately, while the theory was sound, the early intravaginal experiment failed for the simple reason that the animal quickly expelled the probe through muscular action, perhaps involuntary but nevertheless effective to rid her body of the foreign object.

Notwithstanding the foregoing setbacks, it has now been discovered in accordance with the teaching of the instant invention that long term and remotely readable deep body temperature readings that are accurate and virtually unaffected by external conditions can, in fact, be taken intravaginally by the simple yet unobvious, expedient of attaching the temperature probe to an expandable anchor, inserting the probe and anchor deeply within the vaginal canal with the anchor in collapsed condition, permitting the anchor to expand to hold the probe in place despite the muscular actions of the animal in an effort to expel same, interrogating the sensor daily from a remote station at approximately the same time each day for a period of not less than one full estrous cycle, and noting any change in the deep body temperature of the animal during the aforesaid cycle as a means for detecting estrus or the onset of febrile illness.

It is, therefore, the principal object of the present invention to provide a novel and improved method for the remote detection of physiological changes taking place in female mammals.

A second objective is the provision of a method of the type aorementioned wherein surgical invasion of the animal is unnecessary.

Another object of the within described invention is to provide a means for monitoring the body temperature of a female mammal on a long term basis such that the data taken is virtually unaffected by external conditions, stress or other outside factors.

Still another objective is to provide a method of the character described which is sufficiently accurate to enable one to reliably detect both the onset of febrile illness and estrus while, at the same time, permitting the observer to differentiate therebetween.

An additional object is to provide a long term remote temperature sensing method particularly well suited to female farm animals of the bovine, equine and porcine species which is cost-effective and practical under herd management conditions.

Further objects are to provide a body temperature monitoring method for mammalian females which is simple, efficient, dependable safe, relatively inexpensive, long-lasting and one that is easily carried out by unskilled personnel.

Other objects will be in part apparent and in part pointed out specifically in connection with the description of the drawings that follows, and in which:

FIG. 1 is a diagram showing placement of the probe and the anchor therefore in the vagina of the animal; and, FIGS. 2–7 are charts detailing the long term intravaginal temperature response of various species of female mammals.

Referring initially to FIG. 1, the temperature sensing probe 10 used in the instant method is conventional and it consists of a battery powered transmitter containing a temperature-sensing thermistor which sends out a pulsed signal, the rapidity of which corresponds to the temperature of the transmitter and also the deep body temperature of the animal when implanted in her vaginal canal 12. The transmitter 10 has been shown without detail but approximately its actual size in relation to a grown cow's vagina 12. The resulting signal is sensed at a remote location outside the animal's body. The location of the receiver 14 is optional depending upon its sensitivity and the strength of the signal generated, some receivers being responsive to signals originating miles away from the transmitter. The selection of signal strength and receiver sensitivity is a matter of choice well within the skill of the art and will depend to a considerable degree upon several extraneous factors such as the size of the herd, the ability of the equipment to differentiate among the several animals, the degree of confinement of the herd, if any, and other similar parameters.

The signal that is received is recorded and analyzed during a preselected time period, say five minutes, at the same or approximately the same time each day. In bovine animals, for instance, it is a well-known fact that the lowest body temperatures of the day occur early in the morning between approximately 5:00 and 7:00 a.m. The baseline against which the spikes are most evident is likely to be established during such a time period; therefore, for cattle at least, the measurements are preferably made during this minimum baseline temperature interval.

For small confined herds, tunable receivers are unnecessary provided the transmitted signal is relatively weak. In such a circumstance, the receiver is placed in reasonably close proximity to the particular transmitter whose temperature signal is to be decoded so as to screen out other extraneous signals. On the other hand, care should be taken to not excite the animal thus inducing a false spike which is often the case with transponders inserted into a body cavity and removed after such reading in the manner of Mattox and others.

The battery powered radio transmitter 10 containing the temperature-sensitive thermistor is implanted at the mouth of the cervix 16 where, for purposes of making dependable and accurate predictions, it must stay for at least one complete estrous cycle and preferably fifty days or longer. Because of the stress-induced fluctuations in temperature, handling of the animal should be minimized; however, a 50 day test performed at the proper time will allow the animal to settle down while at the same time provide good baseline temperature data against which the spikes become easy to detect as will appear presently. Notwithstanding the long term implantation of the radio transmitter, it remains readily accessible to serve, repair and change batteries, all without having to resort to surgical invasion of the animal or require the services of a D.V.M.

The act of implantation is a simple one using standard techniques and instruments like, for instance, a trochar tube and pushrod or plunger inside the latter. The problems do not arise in connection with placement of the probe but rather with how to keep it in place. The muscle contractions and relaxations of the vaginal walls are such that they quickly eject any foreign object like the probe. The answer came in the form of an expandable anchoring device which is introduced into the vagina in collapsed form and then expanded to provide a multi-fingered element which would yield under the influence of the contracting vaginal muscles thus preventing them from getting a sufficient hold to eject either the anchor or the transmitter attached thereto back out through the vulva. One spider like form of anchor which has been used with good results is shown in FIG. 1 and identified by reference numeral 18. A device having characteristics very much like the anchor shown, but for a different purpose, forms the subject matter of one or more of the following U.S. Pat. Nos. 3,811,423; 3,811,443; 3,811,424; and 4,091,807.

Once the probe is in place as shown, the herd manager or other investigator can begin gathering data for the purpose of ascertaining when the animal is in condition to conceive or, alternatively, is not ovulating and cannot be impregnated. This same data will be effective to indicate the onset of a febrile illness well before any overt clinical signs become apparent. The results of actual deep body temperature measurements in three species of female livestock mammals form the subject matter of the graphs appearing herein as FIGS. 2–7, inclusive, to which detailed reference will soon be made; however, before doing so, it would seem appropriate to digress briefly and explain a bit more about when the probe should be implanted and why it should be kept in place for an extended period of time.

Cows and other female animals are known to have cyclic variations in basal body temperature which cycle bears a relationship to the estrous cycle. This cycle was discovered to differ a great deal from that of the human female. One major difference is the fact that women experience a near constant temperature pattern from period-to-period, whereas, cattle and other animals do not. The fact of the matter is that farm animals exhibit a changing temperature pattern which seems to depend to some degree at least upon the climate and the season. For instance, it can be demonstrated that the normal body temperature baseline takes on an ascending pattern during prolonged periods of cold weather and a descending one when it is warm. It is essential, therefore, that a fairly long term history of not less than a complete estrous cycle and preferably even longer, say 50 days, be kept and used as the basis for detecting any significant changes such as those that signal ovulation or the onset of febrile illness.

In the human female, despite the constant temperature pattern between periods, Mattox found he could not [realiably] *reliably* detect ovulation based upon deviations from this pattern even though he was using highly motivated, intelligent and cooperative women. Nonetheless, and contrary to what one might expect, readily detectable temperature spikes signalling ovulation do occur in farm animals. Even though the baseline temperature varies seasonally and with environmental conditions, it has been discovered in accordance with the teaching of the instant invention that ovulation can be reliably ascertained provided a sufficient temperature history leading up to the anomaly or spike is available. The proof is, of course, that animals bred on such a spike get pregnant while those bred at other times do not.

More specifically, the estrous cycle is such that a pronounced spike in the order of 0.8° C. is noted on the day of estrus in a cow, for example, while an equally prominant dip in temperature takes place on the preceding day and again on the following day when ovulation occurs. This cyclic pattern happens in cows with so-called "silent heats" as well as those with normal heat periods. This 0.8° spike lasts for one day only and it is detected by measuring it against her average body temperature over the preceding ten day period or thereabouts.

In a dairy herd, for example, a cow's greatest milk is produced provided she is inseminated within 90 days after parturition; yet, statistics show that about one-third of all dairy cows miss this target for the reason that over 40% of these cows never have a heat period recorded within the first sixty days after they have calved and an additional 12% or so go over ninety days. Even after the first heat period following parturition is recorded, about one in every six thereafter is missed. For these reasons alone, it is of utmost importance if cost-effective dairy herd management is to be achieved, that each of these heat periods, and preferably the first, is reliably detected.

Figure 2:
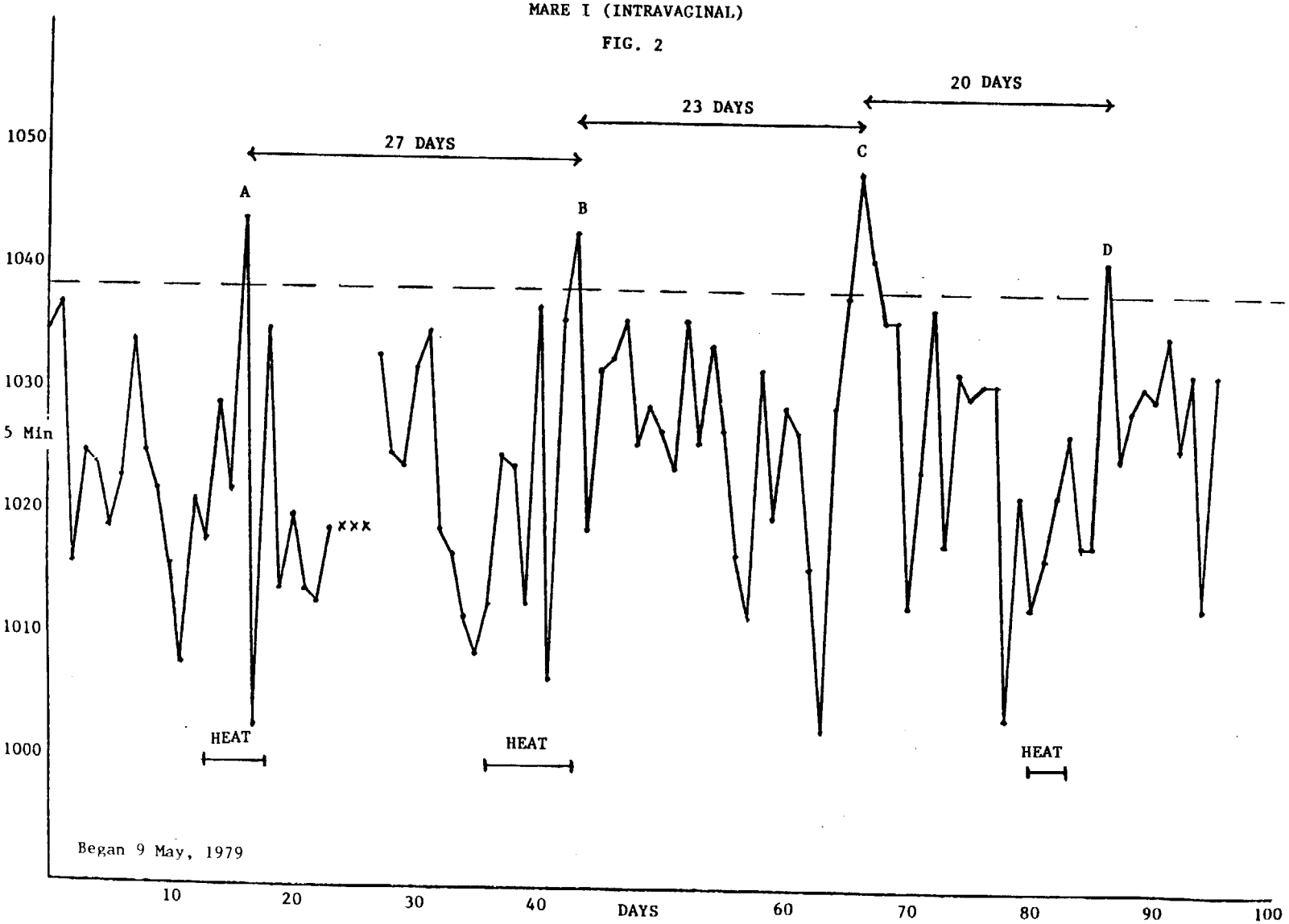

Turning the attention next to the graph of FIG. 2, wherein Mare I showed four spikes (A, B, C and D) that surpassed a threshold line (spike indicates about ¾° C. above mean). These spikes are spaced at regular intervals that coincide with the expected time between ovulations. Also, spikes A, B and D were associated with estrus. The mare was not teased during the period of spike C, so the estrus status is not known. Each data point (dot) represents a once-daily reading taken at approximately 7:30 a.m. between May 9 and Aug. 12, 1979. The ordinate scale is in radio counts per 5 minute period.

Figure 3:
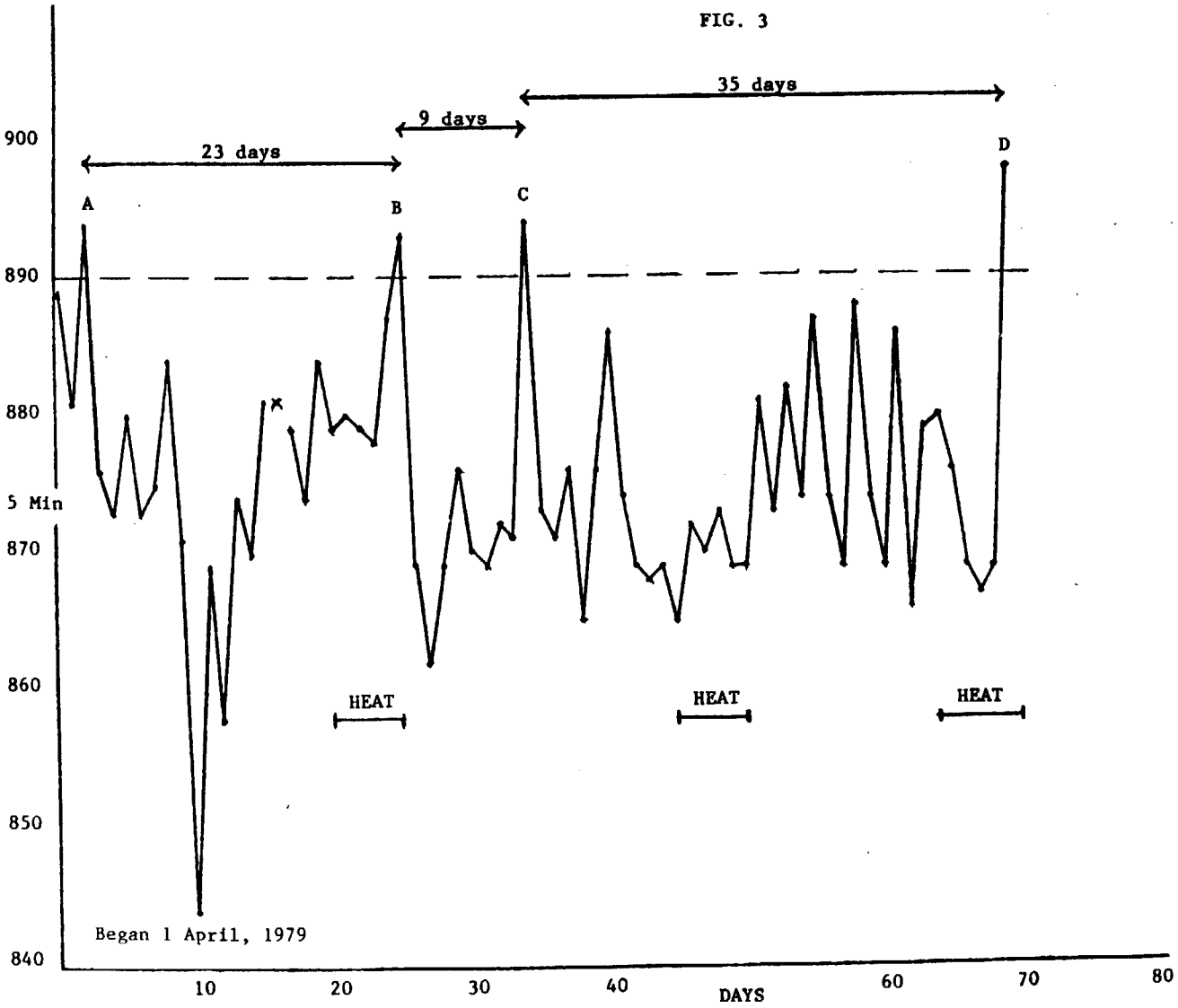

Mare II charted in FIG. 3 showed four substantial temperture spikes (magnitude about ¾° C. above mean) which extend above the threshold line. Spikes B and D occurred at the last day of the estrous period. The mare was not teased during the period of spike A, so her receptivity is not known. The spike C occurred during mid-estrous and, curiously, no spike appeared during the subsequent estrous period. Each data point (dot) represents a once-daily reading taken at approximately 7:30 a.m. between June 1st and Aug. 10, 1979. The left side scale is in radio counts per 5 minute period.

Figure 4:
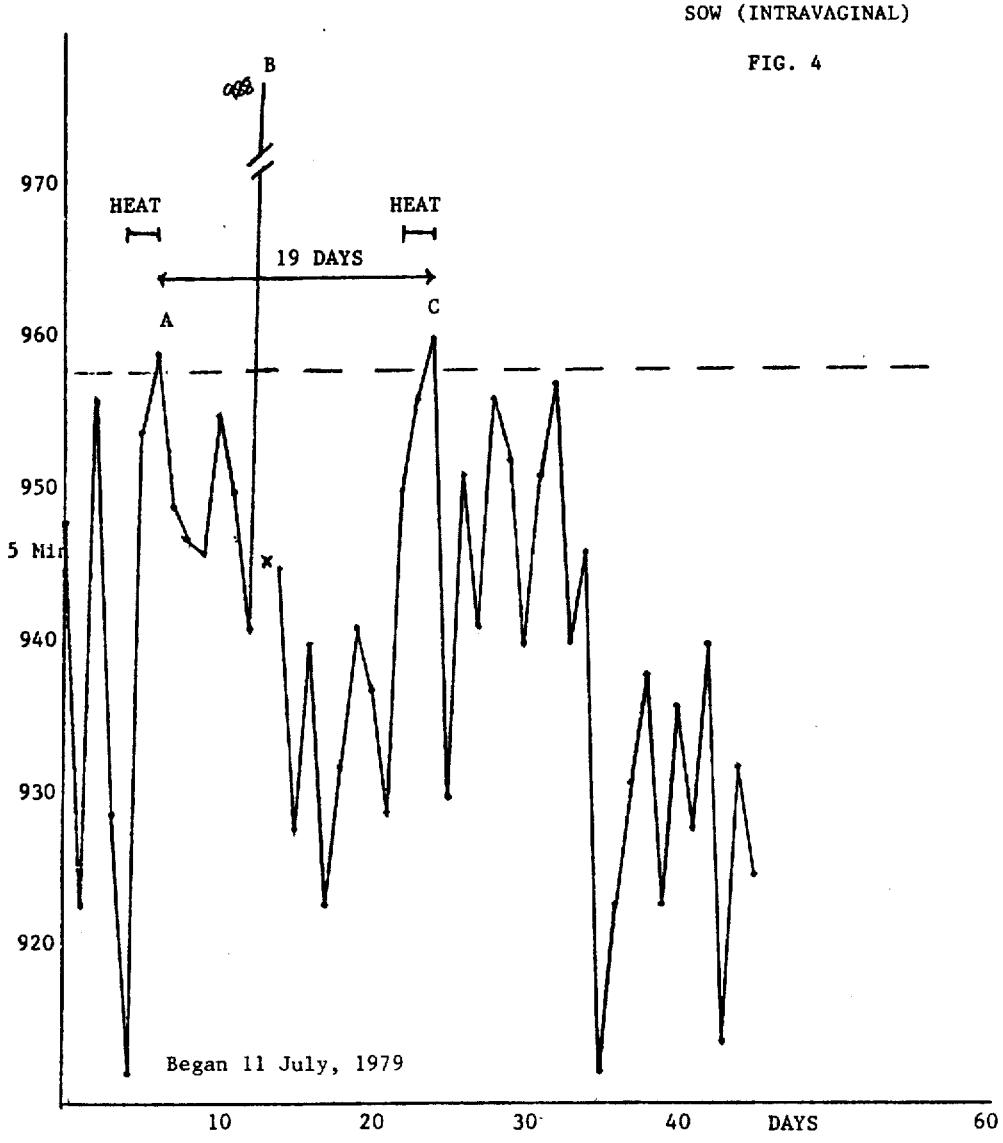

The intravaginal temperature graph of FIG. 4 was taken of a sow instead of a mare. The sow exhibited two heat periods of 2 days duration which is characteristic of sows. There were temperature spikes (A and C) towards the end of each heat period. The sow was accidentally bred on the second day after spike C and became pregnant. Spikes A and C were nineteen days apart which matches exactly the normal ovulation interval for sows. Spike B was quite high and indicates a fever of short duration which might well have been due to a mold infection such as a virus might cause.

Figure 5:
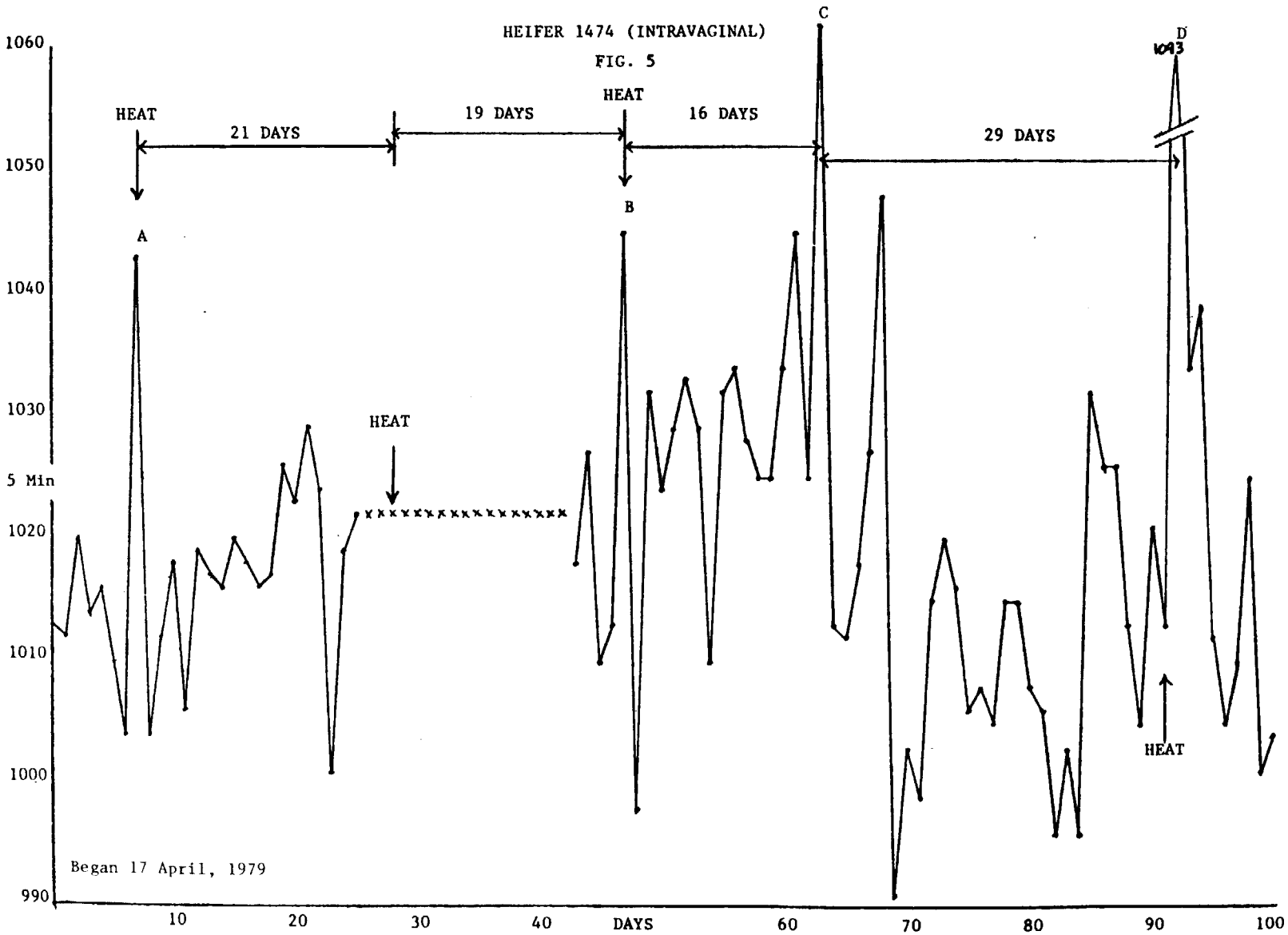

Directing the attention next to FIG. 5, heifer 1474 initially experienced three normal heat periods and there were temperature spikes (A and B) recorded as shown. The transmitter was not implanted in the heifer during the period marked xxx. Spike C was not accompanied by standing heat, however, the interval was normal from the previous spike and the heifer was bred. It is believed that she became pregnant and then miscarried because she came in heat 28 days later with a spike occurring the subsequent morning. The 29 day interval was too long for normalcy. Eventually, the heifer was bred again during a heat and spike episode and she became pregnant.

Figure 6:
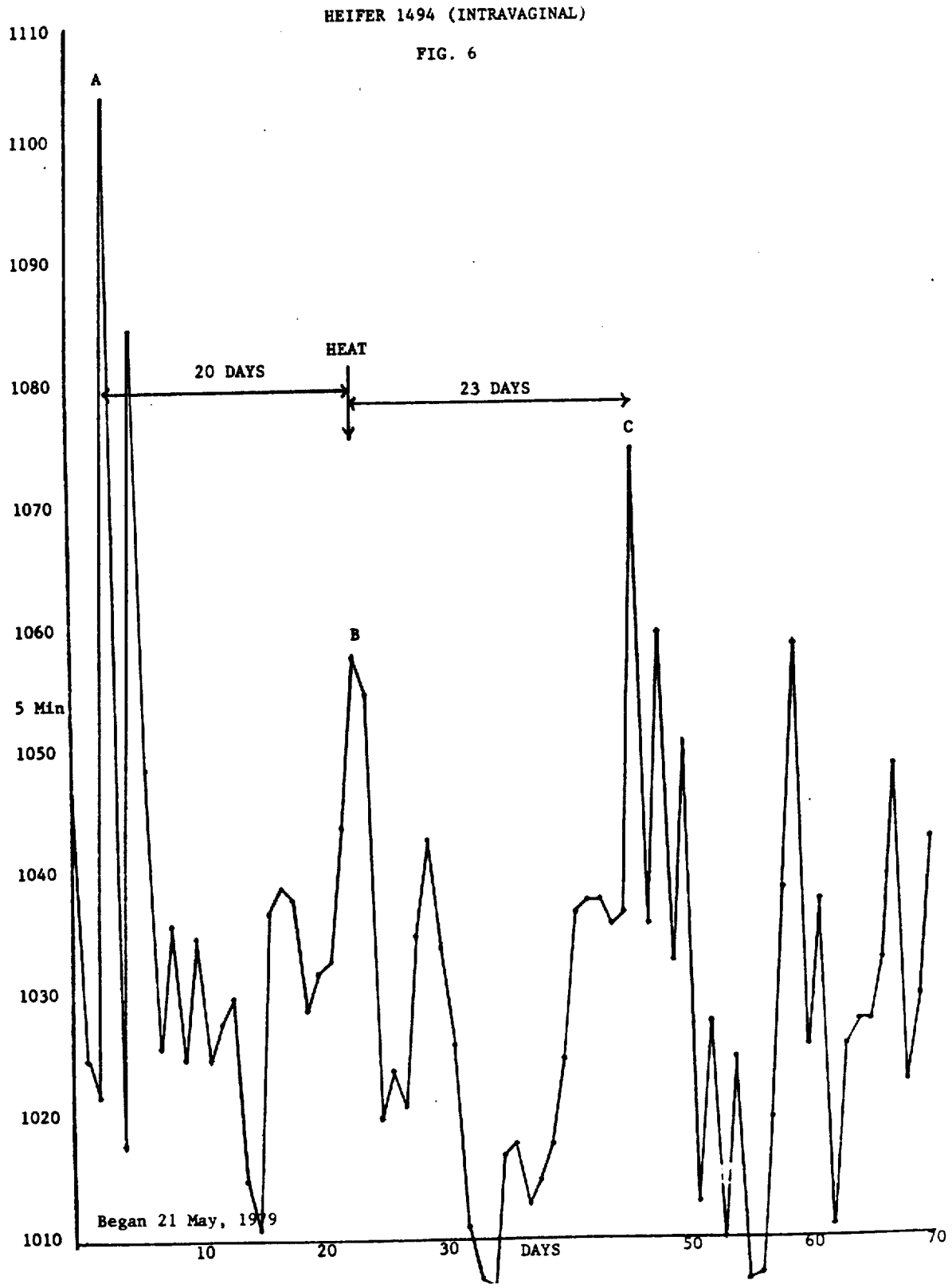

FIG. 6 to which reference will next be made details the temperature pattern of yet another heifer. Heifer 1494 presented spikes A, B and C during her test period. She was just reaching puberty when brought into the experiment. She only expressed heat once and that was accompanied by spike B; nevertheless, she did have normal intervals [beteeen] *between* the three significant spikes. Following spike C she did not show any mating behavior or spikes during a period of very hot weather. Eventually, she did come in heat and had a smaller spike. She was bred and became pregnant.

Figure 7:
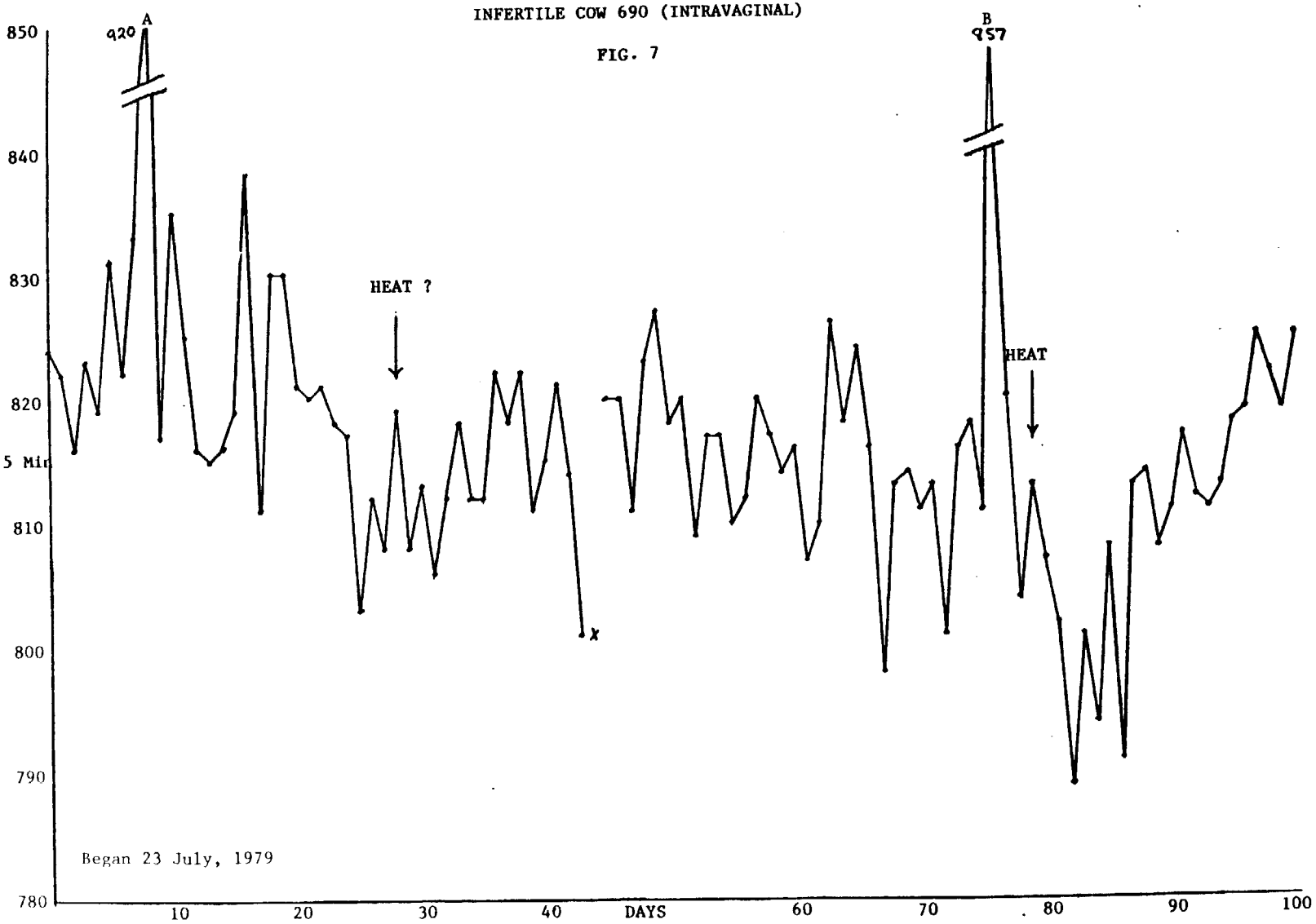

Finally, with reference to FIG. 7, a cow 690 was selected because of her infertility as a subject for examination of spike conditions during known reproductive insufficiency. There were two very high spikes without associated heat. She had a questionable heat once and a definite standing heat towards the end of the observation period. The cow was bred at spike B and did not become pregnant. Apparently, the cow is physiologically out of phase and there was no normal periodicity in her record at all. This example clearly illustrates the value of the remotely-sensed temperature method of the present invention in detecting acyclicity and probable ovulation failure.

On the whole, the foregoing charts clearly reflect the day-to-day physiological conditions of the subjects. When her temperature reading is noticeably greater than her previous ten day average and exceeds all previous highs during that time interval, the probability is that she is preparing to ovulate and she should be bred on either the day of the [estrus] *estrous* spike or early the next day. In the specific case of cows, if the foregoing temperature spike falls on a 21±5 day interval from the preceding spike, the cow is very probably ovulating; however, if the spike is out of phase with the normal estrous cycle as above noted and has a magnitude somewhere around three times the magnitude of previous spikes, the animal is very probably feverish and such a spike signals the onset of some febrile illness rather than estrus and at a time well in advance of when any clinically recognizable symptoms appear. The random occurrence of such spikes their magnitude and duration (more than one day) allow the observer to readily differentiate between the fever spike and the estrus spike. It is also significant to note that the failure to record a spike is equally informative because it signals the absence of ovulation which is every bit as important to know as when the animal is experiencing normal ovulation (see FIG. 7).

The foregoing examples clearly demonstrate that, while the temperature cycles of various species of female farm animals have long been recognized as effective indicators of estrus, until now there has never been a reliable, practical and effective method for determining the animal's temperature, deep body or otherwise, on a daily basis under herd management conditions. The instant method permits the long term monitoring of the deep body temperature of a female mammal without having to handle over and over again. The subject is natural at all times and need not be agitated as is the case with present deep body temperature measurement methods where the thermometer or other types of temperature measurement probe is repeatedly inserted and removed from her rectum or vulva every single day. The animal is not harmed in any way or otherwise traumatized yet she is constantly providing the observer with much needed information on her physical condition which is otherwise essentially unattainable under field conditions.

Summarizing, the instant method solves three heretofore unsolved problems, namely: (1) it provides for remote interrogation and possibly even automated monitoring of an animal's deep body temperature by means of an indwelling probe implanted without surgery; (2) it provides information on ovulation on all animals, both those experiencing active estrus and those who are not; and (3) it detects feverish conditions in advance of clinical illness.

What is claimed is:

1. The improved method for detecting a feverish condition in mammalian females which comprises the steps of: attaching a battery powered radio telemetric temperature measuring device of a size adapted for insertion into the uterine canal to an expandable anchor of approximately the same size in collapsed condition as said telemetry device, collapsing the anchor and inserting it while thus collapsed along with the telemetry device attached thereto the vagina to a depth where the assembly thus formed lies adjacent the cervix, expanding the anchor "in situ", monitoring the temperature daily from a remote external location at approximately the same time each day for a period not less than approximately one complete estrous cycle, and comparing the temperature each day with the average temperature over the immediately preceding approximately ten day period to detect any abrupt changes therein of a magnitude several tenths of a °C. higher than the deviation in temperature upon which said average temperature was determined.

2. The improved method as set forth in claim 1 wherein the temperature is monitored for approximately 50 days.

3. The improved method as set forth in claim 1 wherein the daily temperature reading is taken between approximately 5:00 and 7:00 a.m.

4. The improved method as set forth in claim 1 which includes the step of inseminating the subject no later than one day following the day upon which said abrupt temperature change is detected.

5. The improved method as set forth in claim 1 which includes the step of treating the subject for febrile illness if said abrupt temperature change persists over one day.

*6. A method for detecting ovulation in a female herd animal selected from the bovine, equine and porcine species and subject to climatic temperature variations, said method comprising the steps of:*

*selecting an intravaginal anchor adapted for retention in said animals's vagina for a period not less than one complete estrous cycle of said animal and equipped with a telemetric temperature measuring device for relaying temperature information from the animal to a location of a remote monitoring station;*

*inserting said anchor into the vagina of said herd animal, maintaining said anchor in said vagina for a period of not less than one complete estrous cycle, and locating said animal in an area such that a range of said telemetric measuring device allows said device to relay said information to said station;*

*measuring an intravaginal temperature of said animal at least one time daily at approximately the same time each day for a period not less than one complete estrous cycle of said animal;*

*relaying said information to said remote monitoring station;*

*averaging temperature measurements taken over a plurality of days and comparing a temperature taken on a succeeding day with an average calculated in said averaging step;*

*repeating said averaging and comparing steps on each next succeeding day, the number of days of said plurality of days remaining constant;*

*identifying as a significant elevated temperature a temperature taken on one of said succeeding days that is at least several tenths of a degree Celsius higher than an average of temperatures for a preceding plurality of days and that also exceeds temperatures taken at approximately the same time on said preceding plurality of days;*

*counting a number of days between said significant elevated temperature and a previous temperature spike attributable to a preceding onset of ovulation; and*

*identifying said succeeding temperature as a subsequent onset of ovulation when said counted number of days is within about five days of an average estrous cycle length of said animal.*

*7. The method of claim 6 wherein said period of not less than approximately one complete estrous cycle is approximately 50 days.*

*8. The method of claim 6 wherein said same time is the period between about 5:00 and about 7:00 a.m.*

* * * * *